United States Patent [19]
Robinson

[11] Patent Number: 5,260,309
[45] Date of Patent: Nov. 9, 1993

[54] 4,5,6,11-TETRAHYDROBENZO [6,7] CYCLOOCTA [1,2-B]THIOPHEN-6,11-IMINES AND 6,11-DIHYDROBENZO [6,7] CYCLOOCTA [1,2-B] THIOPHEN-6,11-IMINES

[75] Inventor: Ralph P. Robinson, Gales Ferry, Conn.

[73] Assignee: Pfizer Inc., New York, N.Y.

[21] Appl. No.: 828,892

[22] PCT Filed: Jun. 1, 1989

[86] PCT No.: PCT/US89/02387

§ 371 Date: Jan. 29, 1992

§ 102(e) Date: Jan. 29, 1992

[87] PCT Pub. No.: WO90/15060

PCT Pub. Date: Dec. 13, 1990

[51] Int. Cl.$^5$ .................... C07D 513/22; A61K 31/38
[52] U.S. Cl. .................... 514/215; 540/581
[58] Field of Search .................... 548/421; 514/215; 540/581

[56] References Cited

U.S. PATENT DOCUMENTS

| | | | |
|---|---|---|---|
| 4,112,110 | 9/1978 | Blattner | 424/274 |
| 4,252,810 | 2/1981 | Anderson et al. | 424/256 |
| 4,329,465 | 5/1982 | Anderson et al. | 546/72 |
| 4,414,154 | 11/1983 | Anderson et al. | 260/245.7 |
| 4,981,848 | 1/1991 | Ku | 540/581 |
| 4,996,211 | 2/1991 | Baker et al. | 514/289 |

FOREIGN PATENT DOCUMENTS 0011206 5/1980 European Pat. Off.
WO/15060 12/1990 PCT Int'l Appl.

OTHER PUBLICATIONS

Brenner, et al., *J. Heterocyclic Chem.*, 19, 897 (1982).
Brenner, et al., *J. Heterocyclic Chem.*, 22, 555 (1985).
Brenner, et al., *J. Heterocyclic Chem.*, 23, 1331 (1986).
Lyle, et al., *J. Am. Chem. Soc.*, 109, 7890 (1987).
Robinson, et al., *Tetra. Lett.*, 30 (39), 5203 (1989).
Dennis, et al., *J.C.S. Perkin I*, (1975), 1506.
Nomoto et al., *Heterocycles*, 22 (9), 1969 (1984).
Dygos, *J. Heterocyclic Chem.*, 13, 1355 (1976).
Barcza, et al., *J. Org. Chem.*, 40 (20), 2982 (1975).
Remy et al., *J. Org. Chem.*, 43 (22), 4311 (1978).
Anderson, et al., *J. Org. Chem.*, 44 (9), 1519 (1979).
Christy, et al., *J. Org. Chem.*, 44 (18), 3117 (1979).
Evans, et al., *J. Org. Chem.*, 44 (18), 3127 (1979).
Lamanec, et al., *J. Org. Chem.*, 53 (8), 1769 (1988).
Carpino, et al., *J. Org. Chem.*, 53 (11), 2565 (1988).
Lown, et al., *J. Org. Chem.*, 36 (10), 1405 (1971).

*Primary Examiner*—Nicholas S. Rizzo
*Attorney, Agent, or Firm*—Peter C. Richardson; Paul H. Ginsburg; Grover F. Fuller, Jr.

[57] ABSTRACT

The present invention relates to compounds of the formula

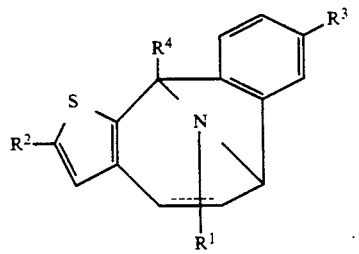

wherein the broken line represents a saturated or an olefinic bond, $R^1$ and $R^4$ are each hydrogen or $C_1$ to $C_6$ alkyl, and $R^2$ and $R^3$ are each hydrogen, $C_1$ to $C_6$ alkyl, halogen, $C_1$ to $C_6$ alkoxy or $C_1$ to $C_6$ alkylthio, and pharmaceutically acceptable salts thereof, pharmaceutical compounds containing the same, methods of preparing the foregoing compounds, and to novel intermediates in the preparation of the foregoing compounds. These compounds are useful as agents in the prevention of neuronal damage in the brain following cerebral ischemia and during the progression of Alzheimer's disease and also as anticonvulsants.

20 Claims, No Drawings

4,5,6,11-TETRAHYDROBENZO [6,7] CYCLOOCTA [1,2-B]THIOPHEN-6,11-IMINES AND 6,11-DIHYDROBENZO [6,7] CYCLOOCTA [1,2-B] THIOPHEN-6,11-IMINES

BACKGROUND OF THE INVENTION

U.S. Pat. No. 4,414,154 refers to compounds of the formula

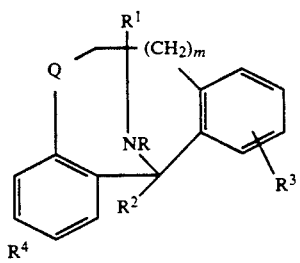

The compounds are said to be useful as anticonvulsants, anxiolytics and antidepressants. The foregoing compounds do not have a thiophene ring as part of the tricyclic ring system.

U.S. Pat. No. 4,252,810 refers to compounds of the formula

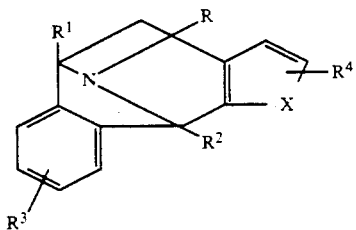

The compounds are said to be useful as antianxiety agents and as muscle relaxants. The compounds of the '810 patent have a different orientation of the thiophene ring than the compounds of the present invention as well as a cyclohepta-rather than a cycloocta-ring as part of the bridged tricyclic ring system.

SUMMARY OF THE INVENTION

The present invention relates to compounds of the formula

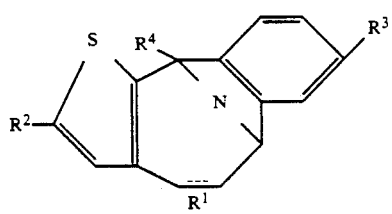

wherein the broken line represents an optional double bond, $R^1$ and $R^4$ are independently selected from hydrogen and $C_1$ to $C_6$ alkyl, and $R^2$ and $R^3$ are independently selected from hydrogen, $C_1$ to $C_6$ alkyl, halogen (e.g., fluoro, chloro, bromo and iodo), $C_1$ to $C_6$ alkoxy and $C_1$ to $C_6$ alkylthio, and pharmaceutically acceptable salts thereof.

Preferred compounds are compounds of the Formula I wherein $R^1$ equals hydrogen. More preferably, $R^1$ equals hydrogen and $R^4$ equals methyl.

Specific preferred compounds of the present invention are the following:

11-methyl-4,5,6,11-tetrahydrobenzo[6,7]cycloocta[2-b]thiophen-6,11-imine;

8-fluoro-11-methyl-4,5,6,11-tetrahydrobenzo[6,7]-cycloocta[1,2-b]thiophen-6,11-imine; and 8,11-dimethyl-4,5,6,11-tetrahydrobenzo[6,7]-cycloocta[1,2-b]thiophen-6,11-imine.

The (+) isomer of 11-methyl-4,5,6,11-tetrahydrobenzo[6,7]cycloocta[1,2,-b]thiophen-6,11-imine is particularly preferred.

The present invention also relates to a pharmaceutical composition for the treatment of cerebral ischemia, Alzheimer's disease or convulsions comprising an amount of a compound of the formula I or a pharmaceutically acceptable salt thereof that is effective in preventing neuronal damage following cerebral ischemia or during the progression of Alzheimer's disease or in preventing convulsions and a pharmaceutically acceptable carrier. Preferred compositions of the present invention contain the foregoing preferred and specific preferred compounds.

The present invention also relates to a method for the treatment of cerebral ischemia, Alzheimer's disease or convulsions, comprising administering an amount of a compound of the formula I or a pharmaceutically acceptable salt thereof that is effective in preventing neuronal damage following cerebral ischemia or during the progression of Alzheimer's disease or in preventing convulsions.

The present invention also relates to a process for the preparation of formula I and pharmaceutically acceptable salts thereof.

The present invention also relates to novel intermediates in the preparation of formula I. Such intermediates are compounds of the formula

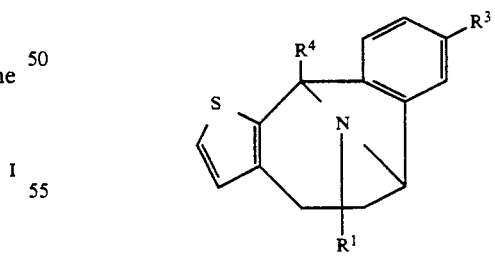

wherein $R^4$ equals hydrogen or methyl, $R^3$ equals hydrogen, fluorine or methyl and $R^1$ is a protecting group such as $CO_2CH_2CCl_3$.

DETAILED DESCRIPTION OF THE INVENTION

The compounds of the present invention may be prepared as shown in the reaction scheme set forth below:

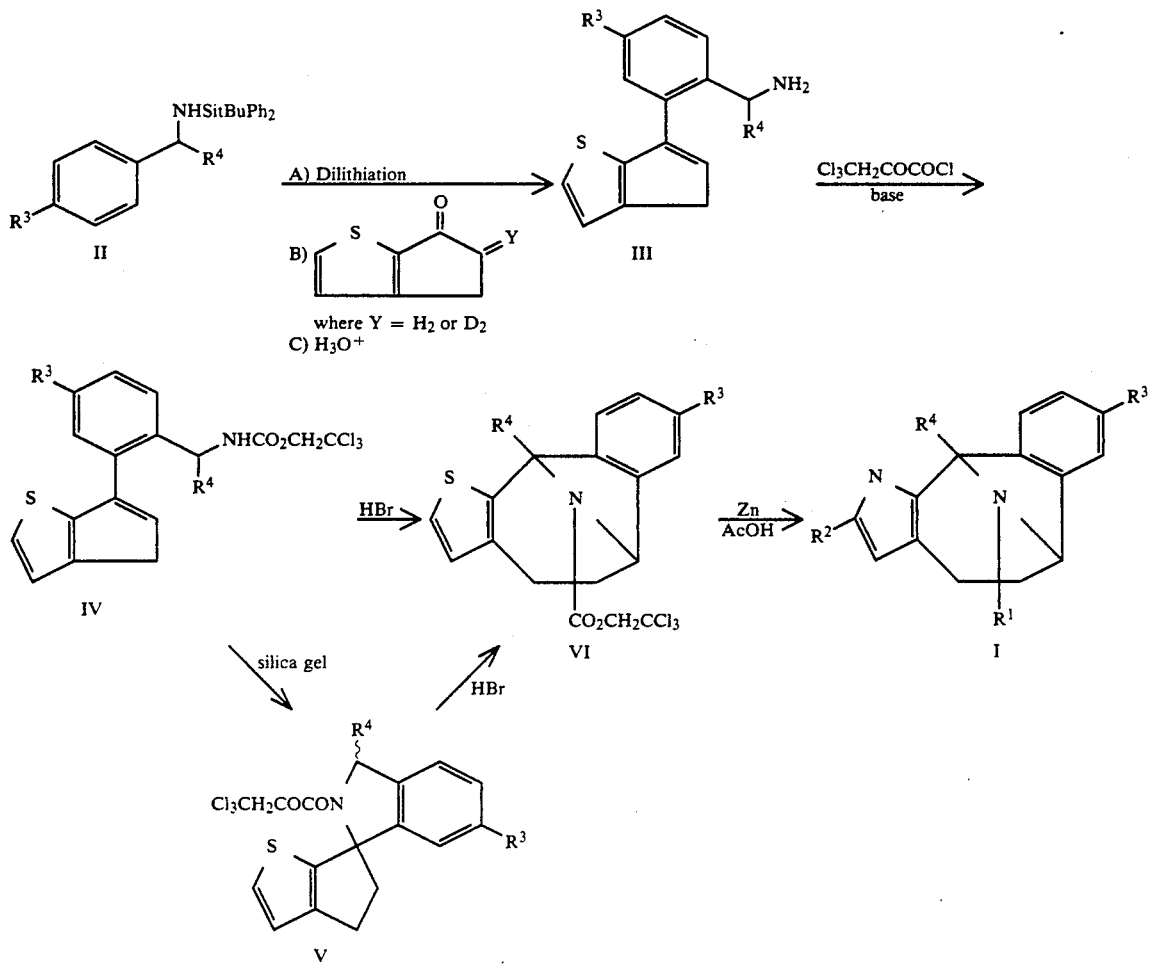

The first step in the sequence involves dilithiation of the appropriate N-silyl benzenemethanamine derivative of Formula II by treatment of Formula II with at least 2 equivalents of an alkyl lithium reagent, preferably commercial n-butyl lithium sold as a solution in hexane. Suitable solvents include anhydrous dialkyl ethers, tetrahydrofuran, saturated hydrocarbons or any combination thereof. To facilitate the lithiation, 0.5 to 1.0 equivalents of tetramethylethylenediamine may be used as a co-solvent. The lithiation process is generally carried out at temperatures ranging from about 0° C. to the boiling point of the solvent being used, although temperatures down to minus 78° C. may be used if desired. When the reaction is carried out at room temperature, a period of about 2 hours is generally allowed for complete dilithiation to take place; longer reaction times (e.g., about 12 hours) are acceptable. The resulting dilithio-N-silyl benzenemethanamine derivative is generally not isolated and can be allowed to react with the appropriate 4,5-dihydro-6H-cyclopenta[b]thiophen-6-one in the same vessel in which the lithiation is carried out. The 4,5-dihydro-6H-cyclopenta[b]thiophen-6-one is typically introduced in solution using an anhydrous inert solvent of the type used in the lithiation process. This step is carried out at external bath temperatures ranging from about minus 100° C. to about 0° C. although minus 78° C. is the preferred temperature. The ensuing reaction is allowed to take place over a period of about 0.5 to about 3 hours. At this point, the reaction mixture is quenched with an excess of saturated $NH_4Cl$ solution and allowed to equilibrate to room temperature. Following dilution with $H_2O$, the mixture is typically extracted twice with diethyl ether. The combined diethyl ether extracts are then concentrated under reduced pressure to remove the solvents. The oily residue is taken up in a mixture of dilute mineral acid and an inert miscible solvent, preferably tetrahydrofuran, and allowed to stir at room temperature over a period of about 2 to about 24 hours; longer times are acceptable. Removal of most of the co-solvent is then carried out under reduced pressure. The remaining residue is diluted with $H_2O$ and is extracted with diethyl ether and the extracts are discarded. By addition of base (typically NaOH, KOH and/or $NaHCO_3$), the pH of the aqueous layer is adjusted to at least 9. The mixture is again extracted twice with ether and the combined extracts are dried over solid $Na_2SO_4$ or $K_2CO_3$. After filtration, the solvent is evaporated under reduced pressure. The residue is typically placed under high vacuum to remove traces of solvent and to remove benezenemethanamine or derivatives thereof. Isolation of the desired compound of Formula III can then be achieved by chromatography on silica gel, generally using a combination of methanol and chloroform as eluant.

The next step of the sequence involves acylation of the appropriate compound of Formula III with 2,2,2-trichloroethylchloroformate and subsequent acid catalyzed rearrangement to the corresponding compound of Formula VI. Thus, under standard acylating conditions, compound of Formula III is generally treated with about 1 to about 1.5 equivalents of 2,2,2-trichloroethylchloroformate in the presence of 1 to 2 equivalents of a tertiary amine, a pyridine or other base soluble in the solvent being used which will not react with 2,2,2-trichloroethylchloroformate. The preferred solvent is dichloromethane, although other solvents, such as chloroform, carbon tetrachloride, benzene, and other aprotic solvents are also suitable. The reaction is generally carried out at 0° C., although temperature as high as the boiling point of the solvent or as low as minus 78° C. can be used. Reaction times ranging from about 5 minutes to several hours may be employed when running the reaction at 0° C. The intermediate N-2,2,2-trichloroethyloxycarbonyl derivative compound of Formula IV need not be isolated when the acylation reaction is run in solvents such as dichloromethane or other halogenated hydrocarbons. In these cases, following completion of the acylation step, the reaction mixture is treated directly with HBr gas which is bubbled through the solution for a period long enough (typically 5 minutes) to achieve complete saturation of the reaction mixture. The preferred temperature for this step is about 0° C.; however other temperatures ranging from minus 78° C. to the boiling point of the solvent can be used. Following introduction of HBr, the reaction is stirred for a time ranging from about 0.5 hour to several days, typically, reaction time is about 2 hours. At this point, the solvent is removed under reduced pressure. The desired compound of Formula VI can then be isolated by liquid chromatography of the residue on silica gel. A mixture of ethyl acetate and hexane is commonly used as the eluant.

An alternative procedure may be followed after completion of the reaction of 2,2,2-trichloroethylchloroformate with the compound of Formula III. This is the preferred method when the acylation step is carried out in solvents other than halogenated hydrocarbons. Thus, when the reaction with 2,2,2-trichloroethylchloroformate is complete, the solvent is removed by evaporation under reduced pressure. The intermediate N-2,2,2-trichloroethyloxycarbonyl derivative of the compound of Formula IV is then isolated, typically by the use of liquid chromatography on silica gel. While carrying out the chromatography on silica gel, acid catalyzed cyclization of the derivative can occur yielding an isomeric spirocyclic amine derivative of the compound of Formula V. Treatment of the spirocyclic compound, the precursor compound of Formula IV or a mixture of the two isomers with HBr gas then proceeds as described above using a halogenated hydrocarbon (e.g., dichloromethane) as solvent.

The final step in the preparation of compounds of Formula I involves removal of the 2,2,2-trichloroethyloxycarbonyl protecting group from the intermediate compound of Formula VI. This can be achieved by the use of standard methods described in the chemical literature. Typically, the compound of Formula VI is dissolved in acetic acid and treated with an excess of zinc powder. The reaction is usually run at about 50° C. although temperatures between the freezing and boiling points of acetic acid may be used. When run at 50° C. reaction times between about 1 and about 24 hours are commonly used. On completion of the reaction, the unreacted zinc is removed by filtration and most of the acetic acid is removed by evaporation under reduced pressure. The residue is taken up in diethyl ether or methyene chloride and washed with $NaHCO_3$ solution, water and brine. The solution is dried ($Na_2SO_4$, $K_2CO_3$, or $MgSO_4$), filtered and evaporated to provide the crude compound of Formula I. Purification is commonly achieved by the use of liquid chromatography on silica gel. The compounds of formula I are often oils but can be converted to crystalline salts by standard methods.

Addition of dilithiated benzenemethanamine derivatives of formula II wherein $R^4$ is other than hydrogen or methyl to 4,5-dihydro-6H-cyclopenta[b]-thiophen-6-one to give compounds of formula III does not take place under the conditions described above. An alternative route to compounds of formula III, wherein $R^4$ is other than hydrogen or methyl is as follows:

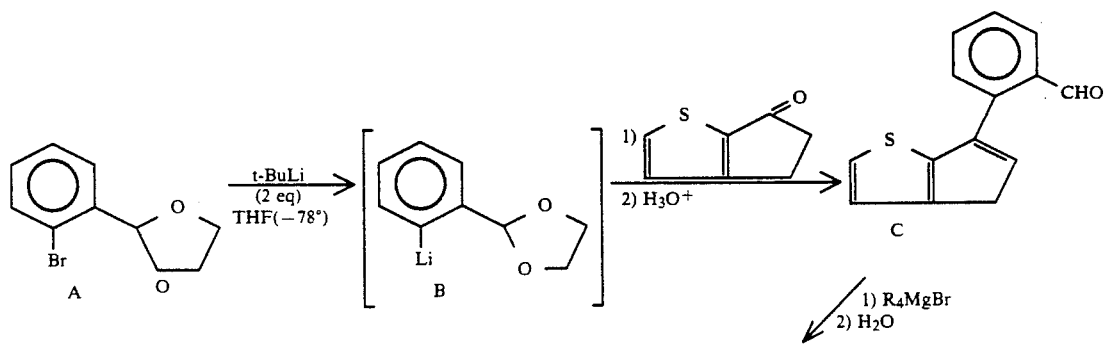

-continued

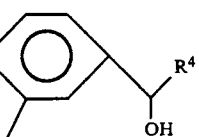
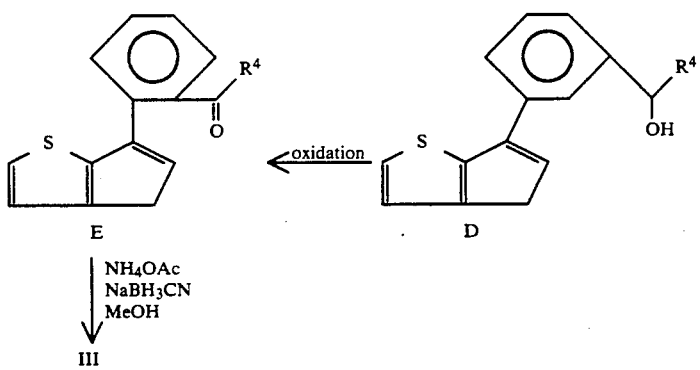

This scheme can be summarized as follows: 2-(2-bromophenyl)-1,3-dioxolane (A) is treated with 2 equivalents of tert-butyl lithium to effect halogen-methyl exchange. The 2-(2-lithiophenyl)-1,3-dioxolane (B) is then reacted in situ with 4,5-dihydro-6H-cyclopenta[b]thiophen-6-one. After aqueous acid workup, 2-(4H-cyclopenta[b]thiophen-6-yl)benzaldehyde (C) is isolated by flash chromatography. This is treated with a Grignard reagent ($R_4MgBr$) to provide the 6-[2-(1-hydroxyalkyl)phenyl]-4H-cyclopenta[b]thiophene (D) which is subsequently oxidized to the 6-[2-(alkylcarbonyl)phenyl]-4H-cyclopenta[b]thiophene (E). Reductive amination of E should then provide compounds of structure III.

The compounds of formula I and their pharmaceutically acceptable salts are effective excitatory amino acid receptor antagonists and are thus useful as agents for the prevention of neuronal damage in the brain. In particular, the compounds are useful for the prevention of neuronal damage following cerebral ischemia and during the progression of Alzheimer's disease. In addition, the compounds function as anticonvulsants.

For the treatment of the various conditions described above, the compounds of the formula I and their pharmaceutically acceptable salts may be administered to a subject in need of treatment by a variety of conventional routes of administration, including oral, topical, rectal, parenteral and by inhalation in aerosol form. In general, these compounds will be administered orally or parenterally at dosages between about 0.01 to about 50 mg/kg of body weight of the subject to be treated per day, preferably from about 0.05 to about 10 mg/kg. However, some variation in dosage will necessarily occur depending on the condition of the subject being treated and the activity of the compound being employed. The person responsible for administration will, in any event, determine the appropriate dose for the individual subject.

The compounds of the formula I and their pharmaceutically acceptable salts may be administered alone or in combination with pharmaceutically acceptable carriers, in either single or multiple doses. Suitable pharmaceutical carriers include inert solid diluents or fillers, sterile aqueous solutions and various organic solvents. The pharmaceutical compositions formed by combining the novel compounds of formula I and the pharmaceutically acceptable carriers are then readily administered in a variety of dosage forms such as tablets, powders, lozenges, syrups, injectable solutions and the like. These pharmaceutical compositions can, if desired, contain additional ingredients such as flavorings, binders, excipients and the like. Thus, for purposes of oral administration, tablets containing various excipients such as sodium citrate, calcium carbonate and calcium phosphate may be employed along with various disintegrants such as starch, alginic acid and certain complex silicates, together with binding agents such as polyvinylpyrrolidone, sucrose, gelatin and acacia. Additionally, sodium lauryl sulfate and talc are often useful for tabletting purposes. Solid compositions of a similar type may also be employed as fillers in soft and hard filled gelatin capsules. Preferred materials for this include lactose or milk sugar and high molecular weight polyethylene glycols. When aqueous suspensions or elixirs are desired for oral administration, the essential active ingredient therein may be combined with various sweetening or flavoring agents, coloring matter or dyes and, if desired, emulsifying or suspending agents, together with diluents such as water, ethanol, propylene glycol, glycerin and combinations thereof.

For parenteral administration, a solution of a compound of the formula I or a pharmaceutically acceptable salt thereof in sesame or peanut oil, aqueous propylene glycol, or in sterile aqueous solution may be employed. Such aqueous solutions should be suitably buffered, if necessary, and the liquid diluent first rendered isotonic with sufficient saline or glucose. These particular aqueous solutions are especially suitable for intravenous, intramuscular, subcutaneous and intraperitioneal administration. In this connection, the sterile aqueous media employed are all readily available by standard techniques known to those skilled in the art.

The activity of the compounds of the formula I as agents for the prevention of neuronal damage in the brain and as anticonvulsants may be determined by a number of standard biological or pharmacological tests. Suitable tests include in vivo tests (such as the prevention of audiogenic seizure in DBA/2 mice and prevention of NMDA-induced seizures in CF-1 mice) as well as in vitro tests (such as displacement of $^3$H-TCP from brain slices and inhibition of NMDA-induced cyclic-GMP).

The present invention is illustrated by the following examples. It will be understood, however, that the invention is not limited to the specific details of these examples.

Reactions requiring anhydrous conditions were carried out in flame-dried glassware under an atmosphere of nitrogen. For reactions utilizing n-BuLi (n-butyllithium) as base, ether was freshly distilled from $LiAlH_4$ and anhydrous THF (tetrahydrofuran) was used from freshly opened bottles. Other solvents and chemicals were used as supplied from the manufacturers without further purification. 4,5-dihydro-6H-cyclopenta[b]thiophen-6-one was prepared as described by MacDowell et al., *J. Org. Chem.*, 32, 1226 (1967). 4-fluoro-α-methylbenzenemethanamine and α,4-dimethyl-benzenemethanamine were prepared as described by de Roocker and de Radzitsky, *Bull. Soc. Chim. Belges*, 72, 195 (1963). Melting points are uncorrected. All NMR spectra were recorded using $CDCl_3$ as solvent. The NMR data are reported in parts per million (δ) and are referenced to the deuterium lock from the sample solvent. Flash chromatography was carried out as described by Still et al., *J. Org. Chem.*, 923 (1978) using 32–63 μm silica gel.

EXAMPLE 1

N-t-Butyldiphenylsilyl-benzenemethanamine

To a solution of benzenemethanamine (21.8 mL, 0.20 mol) and triethylamine (41.2 mL, 0.30 mol) in acetonitrile (400 mL) was added dropwise t-butylchlorodiphenylsilane (52 mL, 0.20 mol). The mixture was stirred at room temperature for 3 hours and then filtered to remove the insoluble white precipitate (triethylamine hydrochloride). After removal of the solvent in vacuo, the crude product was taken up in a 4:1 mixture of ether/hexane and washed sequentially with $H_2O$, saturated $NaHCO_3$ solution and $H_2O$. The solution was dried ($Na_2SO_4/K_2CO_3$) and concentrated to leave an oil which was distilled under high vacuum. The major fraction consisting of the pure product (45.9 g, 66%) distilled from 140° to 160° C. at about 0.1–0.2 mm Hg and crystallized on standing at room temperature, m.p. 34°–36° C.

$^1$H NMR: δ 7.84–7.72 (m, 4H), 7.50–7.28 (m, 11 H), 3.98 (d, J=8 Hz, 2 H), 1.28 (br m, 1 H), 1.10 (s, 9 H).

EXAMPLE 2

6-[2-(Aminomethyl)-phenyl]-4H-cyclopenta[b]thiophene

A solution of the title compound of Example 1 (3.45 g, 10.0 mmol) and N,N,N',N'-tetramethylethylenediamine (0.75 mL, 5.0 mmol) in dry ether (70 ml) was cooled to 0° C. and treated with a solution of n-BuLi (2.5M) in hexane (8.0 mL, 20 mmol). The mixture was stirred at 0° C. for 0.25 hours and then at room temperature for an additional 3 hours. At this point the mixture was cooled to −78° C. A solution of 4,5-dihydro-6H-cyclopenta[b]thiophen-6-one (1.5 g, 10.8 mmol) in dry THF (15 ml) was then added dropwise and the resulting mixture was stirred at 78° to −60° C. over 1 hour. The reaction was quenched by addition of saturated $NH_4Cl$ solution and was allowed to warm to room temperature. The mixture was diluted with ether and $H_2O$. The ether layer was separated and concentrated to leave an oil which was taken up in a mixture of 1N HCl (70 mL) and THF (105 mL). The resulting solution was stirred at room temperature overnight. The mixture was then diluted with $H_2O$ and extracted twice with ether. The extracts were set aside for later recovery of unreacted ketone while the aqueous layer was made basic by addition of solid NaOH and extracted twice again with ether. These extracts were combined, dried ($Na_2SO_4$) and concentrated in vacuo to leave a dark oil. This was placed under high vacuum and warmed at 50° C. for 1 hour to remove benzenemethanamine leaving 540 mg (23%) of the title compound. An NMR spectrum of this material showed it to be of sufficient purity to use directly in the next step. In other runs of this reaction, however, this material could be purified by flash chromatography on $SiO_2$ using successively 1) $CHCl_3$ and 2) 10% $MeOH/CHCl_3$ as eluants.

$^1$H NMR: δ 7.46–7.42 (m, 2 H), 7.36–7.16 (m, 3 H), 7.07 (d, J=4.5 Hz, 1H), 6.44 (t, J=2 Hz, 1 H), 4.94 (s, 2 H), 3.40 (d, J2 Hz, 2 H).

MS: m/z (relative percent) 227 (82), 212 (62), 209 (77), 85 (100). Exact mass calculated for $C_{14}H_{13}NS$: 227.0769. Found: 227.0754.

EXAMPLE 3

4,5,6,11-Tetrahydrobenzo[6,7]cycloocta[1,2-b]thiophen-6,11-imine-12-carboxylic acid-2,2,2-trichloroethyl ester To a solution of the title compound of Example 2 (540 mg, 2.37 mmol) and 4-dimethylaminopyridine (579 mg, 4.74 mmol) in $CH_2Cl_2$ (50 mL) at 0° C. was added 2,2,2-trichloroethylchloroformate (0.49 mL, 3.56 mmol). After stirring at 0° C. for 0.25 hour, HBr gas was bubbled through the solution to achieve saturation. Stirring at 0° C. was continued for 1 hour and at room temperature for a further 0.5 hour. The solvent was removed in vacuo and the residue was subjected to flash chromatography on silica gel using $CHCl_3$ as eluant. All product fractions were combined and concentrated to leave an amber oil. A $^1$H NMR spectrum of this material showed it to consist of a mixture of the bridged desired product and the unrearranged spirocyclic intermediate in a ratio of about 3:1. Thus the mixture was again taken up in $CH_2Cl_2$ (50 ml). The resulting solution was cooled to 0° C. and saturated with HBr gas. After stirring at 0° C. for 0.5 hour and at room temperature for a further 1 hour, the volatiles were removed in vacuo. The residue was subjected to flash chromatography on silica gel using 10% EtOAc (ethyl acetate)/hexanes as eluant. Fractions containing only the title compound were combined and concentrated in vacuo to afford a clear oil (660 mg, 69%).

$^1$H NMR: δ 7.34–7.10 (m, 4 H), 6.95–6.91 (m, 1 H), 6.66 (d, J=5 Hz, 1 H), 6.02 (s, 0.6 H), 5.99 (s, 0.4 H), 5.53–5.47 (m, 1 H), 4.78 (d, J=12 Hz, 0.6 H), 7.73 (s, 0.8 H), 4.61 (d, J=12 Hz, 0.6 H), 2.70–2.61 (m, 1 H), 2.49–2.37 (m, 1 H), 2.14–2.00 (m, 1 H), 1.98–1.84 (m, 1 H).

IR: ($CHCl_3$) 1712, 1414, 1121 $cm^{-1}$.

MS: m/z (relative percent) 403 (65), 401 (65), 254 (22), 226 100), 211 (65), 210 (94), 184 (48). Exact mass calculated for $C_{17}H_{14}$ $^{35}Cl_3NO_2S$: 400.9837. Found: 400.9824.

EXAMPLE 4

4,5,6,11-Tetrahydrobenzo[6,7]cycloocta[1,2-b]thiophen-6,11-imine

To a solution of the title compound of Example 3 (600 mg, 1.49 mmol) in glacial acetic acid (30 ml) was added zinc powder (974 mg, 14.9 mmol). The mixture was stirred under nitrogen in an oil bath at 50° C. overnight and then cooled to room temperature. The mixture was filtered through diatomaceous earth[Celite (trademark)] (washing with $CH_2Cl_2$) to remove excess zinc and concentrated. The oily residue was diluted with $CH_2Cl_2$ and washed twice with saturated $NaHCO_3$ solution and once with brine. The solution was dried ($MgSO_4$) and concentrated in vacuo. The crude product was subjected to flash chromatography on silica gel using 25% EtOAc/hexanes as eluant. Fractions containing the desired product were combined and concentrated to afford an oil (230 mg, 68%).

$^1$H NMR: δ 7.31–7.10 (m, 4 H), 6.88 (d, J=5 Hz, 1 H), 6.69 (d, J=5 Hz, 1 H), 5.28 (s, 1 H), 4.80 (t, J=3 Hz, 1 H), 2.62 (dt, J=15, 3 Hz, 1 H), 2.42 (br s, 1 H), 2.18–1.86 (m, 3 H).

$^{13}$C NMR: δ 142.4, 142.3, 141.6, 136.4, 131.5, 127.6, 122.2, 122.5, 121.8, 120.3, 63.1, 60.9, 37.1, 25.6.

MS: m/z (relative percent) 227 (100), 212 (81).

A sample of the hydrobromide salt was prepared by addition of HBr in ether to an ice cold solution of the amine in ether containing a small amount of MeOH; m.p. 268–274 (dec.). Analysis calculated for $C_{14}H_{14}BrNS$: C, 54.55; H, 4.58; N, 4.54. Found: C, 54.20; H, 4.39; N, 4.37.

The structure of this compound was unambiguously determined by X-ray crystallographic analysis of the hydrobromide salt.

EXAMPLE 5

5,5-Dideutero-4,5-dihydro-6H-cyclopenta[b]thiophen-6-one

To a solution of 4,5-dihydro-6H-cyclopenta[b]thiophen-6-one (10.4 g, 75 mmol) in dry benzene (100 mL) was added solid $K_2CO_3$. The mixture was heated to reflux under nitrogen, $CD_3OD$ (10 g) was carefully added, and heating at reflux was continued for 1 hour. After fitting a distillation head to the reaction flask, methanol was removed by heating until the temperature of the distillate reached 77° C. Another portion of $CD_3OD$ was then added, the reflux condenser was refitted and heating at reflux was resumed for 0.5 hour. This process was repeated two more times. After the final removal of methanol, the dark purple mixture was diluted with $CH_2Cl_2$, treated with activated charcoal and filtered through diatomaceous earth [Celite (trademark)]. The resulting clear solution was concentrated in vacuo to leave a light yellow solid (10.5 g, 100%).

$^1$H NMR: δ 7.87 (d, J=4.5 Hz, 1 H), 7.02 (d, J=4.5 Hz, 1 H), 3.02 (s, 2 H).

EXAMPLE 6

N-t-Butyldiphenylsilyl-α-methyl-benzenemethanamine

To a solution of racemic α-methyl-benzenemethanamine (24.2 g, 0.2 mol) and triethylamine (42 mL, 0.30 mol) in acetonitrile (400 mL) in a flame-dried flask under nitrogen was added dropwise t-butylchlorodiphenylsilane (47 mL, 0.18 mol). The mixture was stirred at room temperature for 3 hours and then filtered to remove the insoluble white precipitate (triethylamine hydrochloride). After removal of the solvent in vacuo, the crude product was taken up in ether and washed sequentially with $H_2O$, saturated $NaHCO_3$ solution and brine. The solution was dried ($Na_2SO_4/K_2CO_3$) and concentrated to leave a clear oil which was distilled under high vacuum. The major fraction consisting of the pure title compound (30.5 g, 47%) distilled from 160° to 165° C. at about 0.4 mm Hg.

$^1$H NMR: δ 7.80 (m, 2 H), 7.60 (m, 2 H), 7.50–7.16 (m, 10 H), 4.01 (m, 1 H), 1.44 (br s, 1H), 1.39 (d, J=6.5 Hz, 3 H), 1.09 (s, 9 H).

EXAMPLE 7

6-[2-(1-Aminoethyl)-phenyl]-4H-cyclopenta[b]thiophene

A solution of the compound of Example 8 (7.3 g, 20.3 mmol) and N,N,N',N'-tetramethylethylenediamine (1.65 mL, 10.9 mmol) in dry ether (120 ml) was cooled to 0° C. and treated with a solution of n-BuLi (2.5M) in hexane (17.5 mL, 43.8 mmol). The mixture was stirred at 0° C. for 0.5 hour and then at room temperature for an additional 1.5 hours. At this point the mixture was cooled to −78° C. A precooled solution of the compound of Example 5 (2.63 g, 18.8 mmol) in dry THF was then added by direct transfer via canula and the resulting mixture was stirred at −78° to −60° C. over 0.5 hour. The reaction was quenched by addition of saturated NH₄Cl solution (40 mL) and was allowed to warm to room temperature. The mixture was diluted with ether and $H_2O$. The ether layer was separated and concentrated to leave an oil which was taken up in a mixture of 1N HCl (200 mL) and THF (250 mL). The resulting solution was stirred at room temperature overnight. Following removal of most of the THF in vacuo, the solution was extracted twice with ether. The extracts were set aside for later recovery of unreacted compound of Example 5 while the aqueous layer was made basic by addition of solid NaOH and extracted twice again with ether. These extracts were combined, dried ($Na_2SO_4$) and concentrated in vacuo to leave a red oil. This was placed under high vacuum, warmed to remove α-methyl-benzenemethanamine and subjected to flash chromatography on silica gel. The column was initially eluted with $CHCl_3$ to remove unwanted nonpolar impurities. Subsequent elution with 2% and then 5% $MeOH/CHCl_3$ provided, after removal of the solvents, the title compound (1.19 g, 26%).

$^1$H NMR: (300 MHz) δ 7.68–7.58 (m, 1 H), 7.44–7.18 (m, 4 H), 7.10 (d, J=4.5 Hz, 1 H), 6.37 (t, J=2 Hz, 0.7 H), 4.46 (q, J=6.5 Hz, 1 H), 3.39 (d, J=2 Hz, 2 H), 1.65 (br s, 2 H), 1.33 (d, J=6.5 Hz, 3 H).

$^{13}$C NMR (75 Mz) δ 147.8, 147.4, 146.0, 140.8, 133.9, 132.1, 129.0, 128.6, 126.8, 125.6, 122.5, 46.9, 35.8, 25.6.

MS: m/z (relative percent) 242 (37), 241 (61), 223 (48), 209 (100), 208 (94), 113 (52). Exact mass calculated for $C_{15}H_{15}NS$: 241.0926. Found: 241.0927.

EXAMPLE 8

11-Methyl-4,5,6,11-tetrahydrobenzo[6,7]cycloocta-[1,2-b]thiophen-6,11-imine-12-carboxylic acid-2,2,2-trichloroethyl ester To a solution of the compound of Example 7 (1.17 g, 4.38 mmol) and 4-dimethylaminopyridine (0.88 g, 7.20 mmol) in $CH_2Cl_2$ (75 ml) at 0° C. was added 2,2,2-trichloroethylchloroformate (0.83 mL, 6.06 mmol). After stirring at 0° C. for 1 hour, HBr gas was bubbled through the solution to achieve saturation. Stirring at 0° C. was continued for an additional 1.75 hours at which point the solvent was removed in vacuo. The residue was dissolved in a minimum amount of $CH_2Cl_2$ and subjected to flash chromatography on silica gel using 20% EtOAc/hexane as eluant. Fractions containing the desired product were combined, concentrated, and again subjected to flash chromatography on silica gel using 10% EtOAc/hexanes as eluant. Fractions containing only the desired product were combined and concentrated to provide the pure title compound (1.23 g, 61%) as a clear oil. Impure fractions were combined, concentrated and placed on a third column. This was eluted with 5% EtOAc/hexanes to afford an additional amount of pure carbamate (0.35 g, 18%).

$^1$H NMR: δ 7.36–7.24 (m, 3 H), 7.14–7.04 (m, 1 H), 6.94 (d, J=5 Hz, 0.6 H), 6.90 (d, J=5 Hz, 0.4 H), 6.68–6.60 (m, 1 H), 5.56 (br s, 0.6 H), 5.52 (br s, 0.4 H), 4.84 (d, J=12 Hz, 0.4 H), 4.75 (d, J=12 Hz, 0.6 H), 4.67 (d, J=12 Hz, 0.6 H), 4.63 (d, J=12 Hz, 0.4 H), 2.70–2.46 (m, 2 H), 2.36 (s, 1.2 H), 2.35 (s, 1.8 H), 2.10–1.75 (m, 2 H).

IR: (CHCl$_3$) 1720, 1400, 1350, 1295, 1135 cm$^{-1}$.

MS: m/z (relative percent) 417 (10), 415 (12), 240 (41), 223 (25), 224 (100), 198 (44), 131 (38), 97 (57), 95 (49). Exact mass calculated for C$_{18}$H$_{16}$ $^{35}$Cl$_3$NO$_2$S: 414.9967. Found: 414.9815.

EXAMPLE 9

11-Methyl-4,5,6,11-tetrahydrobenzo[6,7]cycloocta-[1,2-b]thiophen-6,11-imine

To a solution of the compound of Example 8 (659 mg, 1.58 mmol) in glacial acetic acid (25 ml) was added zinc powder (994 mg, 15.2 mmol). The mixture was stirred under nitrogen in an oil bath at 55° C. overnight and then cooled to room temperature. The mixture was filtered through diatomaceous earth [Celite (trademark)] (washing with CH$_2$Cl$_2$) to remove excess zinc and concentrated. The oily residue was diluted with CH$_2$Cl$_2$ and washed twice with saturated NaHCO$_3$ solution and once with brine. The solution was dried (MgSO$_4$) and concentrated in vacuo. The crude product was subjected to flash chromatography on silica gel using 25% EtOAc/hexanes as eluant. Fractions containing the title compound were combined and concentrated to afford a slightly yellow oil (276 mg, 72%).

$^1$H NMR: δ 7.27–7.21 (m, 3 H), 7.07–7.04 (m, 1 H), 6.88 (d, J=5 Hz, 1 H), 6.67 (d, J=5 Hz, 1 H), 4.80 (t, J=3 Hz, 1 H), 2.64 (dt, J=15, 3 Hz, 1 H), 2.35 (br s, 1 H), 2.18–1.84 (m, 3 H), 1.97 (s, 3 H).

$^{13}$C NMR: δ 148.1, 145.1, 142.8, 137.6, 131.7, 127.8, 127.0, 121.7, 121.2, 119.5, 65.2, 62.6, 36.8, 26.7, 26.0.

A sample of the hydrobromide salt was prepared by addition of a solution of HBr in ether to an ice cold solution of the amine in ether. The precipitate was recrystallized from a mixture of ether and methanol; m.p. greater than 250° C.

Analysis calculated for C$_{15}$H$_{16}$BrNS: C, 55.90; H, 5.00; N, 4.35. Found: C, 55.79; H, 5.02; N, 4.38.

Similarly a sample of the hydrochloride salt was prepared in ether at 0° C. and was recrystallized from ether/methanol; m.p. 265°–268° C.

MS: m/z (relative percent) 241 (100), 226 (44).

Analysis calculated for C$_{15}$H$_{16}$ClNS · ½ H$_2$O: C, 62.81; H, 5.97; N, 4.88. Found: C, 62.35; H, 5.45; N, 4.59.

EXAMPLE 10

11-Methyl-4,5,6,11-tetrahydrobenzo[6,7]cycloocta-[1,2-b]thiophen-6,11-imine-12-carboxylic acid-1,1-dimethylethyl ester To a solution of the compound of Example 9 (205 mg, 0.85 mmol) in CH$_2$Cl$_2$ (10 ml) was added a solution of di-t-butyldicarbonate (250 mg, 1.15 mmol). The mixture was stirred at room temperature for six days. After evaporation of the solvent, the residue was subjected to flash chromatography on silica gel using sequentially 5% and 10% EtOAc/hexanes as eluants. Fractions containing the title compound were combined and concentrated to leave an oil (242 mg, 83%).

$^1$H NMR: δ 7.25–7.23 (m, 3 H), 7.06–7.03 (m, 1 H), 6.89 d, J=5 Hz, 1H), 6.62 (d, J=5 Hz, 1H), 5.38 (br s, 0.7 H), 5.32 (br s, 0.3 H), 2.62–2.52 (m, 2 H), 2.30 (s, 0.9 H), 2.20 (s, 2.1 H), 1.84–1.68 (m, 2 H), 1.42 (s, 2.7 H), 1.33 (s, 6.3 H).

EXAMPLE 11

2,11-Dimethyl-4,5,6,11-tetrahydrobenzo[6,7]cycloocta-[1,2-b]thiophen-6,11-imine-12-carboxylic acid-1,1-dimethylethyl ester To a solution of the compound of Example 10 (100 mg, 0.293 mmol) in dry THF (5 ml) at −78° C. was added a solution of n-BuLi (2.5M) in hexane (0.14 ml, 0.35 mmol). The solution was stirred at −78° C. for 0.5 hour. An additional quantity of n-BuLi in hexane (0.14 ml, 0.35 mmol) was added and stirring at −78° C. was continued further for 1 hour. The solution was then treated with dimethyl sulfate (99 μl, 1.05 mmol). After stirring at −78° C. for 0.5 hour, the solution was stirred at room temperature overnight and concentrated in vacuo. The residue was taken up in EtOAc and the solution was washed successively with saturated NH$_4$Cl solution, H$_2$O and brine. After drying (Na$_2$SO$_4$), the solution was concentrated to leave a viscous oil which was subjected to flash chromatography on silica gel using 5% EtOAc/hexanes as eluant. Fractions containing only the title compound were combined and concentrated in vacuo to leave an oil (40 mg, 38%).

$^1$H NMR: δ 7.26–7.20 (m, 3 H), 7.08–7.02 (m, 1H), 6.29 (s, 1 H), 5.36 (br s, 0.6 H), 5.30 (br s, 0.4 H), 2.60–2.40 (m, 2 H), 2.34 (s, 3H), 2.26 (s, 1.2 H), 216 (s, 1.8H), 1.86–1.56 (m, 2H), 1.44 (s, 3.6 H), 1.36 (s, 5.4 H).

EXAMPLE 12

2,11-Dimethyl-4,5,6,11-tetrahydrobenzo[6,7]cycloocta-[1,2-b]thiophen-6,11-imine

A solution of the compound of Example 11 (40 mg, 0.113 mmol) in CH$_2$Cl$_2$ (5 ml) at 0° C. was perfused with HBr gas and then stirred at 0° C. for 0.5 hour. Following removal of HBr and CH$_2$Cl$_2$ in vacuo, the residue was taken up in EtOAc and successively washed twice with saturated NaHCO$_3$ solution, once with brine. The resulting solution was dried (Na$_2$SO$_4$) and concentrated to leave the crude title compound as a dark brown oil.

$^1$H NMR: (partial) δ 7.28–7.20 (m, 3 H), 7.08–7.04 (m, 1 H), 6.35 (s, 1 H), 4.88 (t, J=3 Hz, 3 H), 2.34 (s, 3 H), 1.98 (s, 3 H).

The crude product was subjected to flash chromatography on silica gel using EtOAc as eluant. Fractions containing only the desired product were combined and concentrated to leave a brown oil. This was taken up in MeOH and the solution was treated with HCl gas. After removal of the solvent and excess HCl in vacuo, the hydrochloride salt was dissolved in H$_2$O. The solution was filtered through a 22 μm Millipore filter and freeze-dried to yield the hydrochloride salt as a pale tan solid (20 mg, 61%).

MS: m/z (relative percent) 255 (100). Exact mass calculated for C$_{16}$H$_{17}$NS: 255.1081. Found: 255.1058.

EXAMPLE 13

2-Methylthio-11-methyl-4,5,6,11-tetrahydrobenzo[6,7]-cycloocta[1,2-b]thiophen-6,11-imine-12-carboxylic acid-1,1-dimethylethyl ester To a solution of the compound of Example 10 (200 mg, 0.586 mmol) in dry THF (7 ml) at −78° C. was added a solution of n-BuLi (2.5M) in hexane (0.56 ml, 1.40 mmol). The solution was stirred at −78° C. for 1 hour and was then treated with freshly distilled methyl disulfide (125 μl, 1.39 mmol). After stirring at −78° C. for 0.5 hour the solution was stirred at room temperature overnight and quenched with saturated NH₄Cl solution. The mixture was diluted with EtOAc and the organic layer was washed successively with H₂O and brine. After drying (MgSO₄), the solution was concentrated to leave a viscous oil which was subjected to flash chromatography on silica gel using 5% EtOAc/hexanes as eluant. Fractions containing only the desired title compound were combined and concentrated in vacuo to leave an oil (134 mg, 59%).

$^1$H NMR (partial) δ 7.30–7.20 (m, 3 H), 7.08–7.02 (m, 1 H), 6.66–6.60 (m, 1 H), 5.37 (br s, 0.7 H), 5.31 (br s, 0.3 H).

EXAMPLE 14

2-Methylthio-11-methyl-4,5,6,11-tetrahydrobenzo[6,7]-cycloocta[1,2-b]thiophen-6,11-imine A solution of the compound of Example 13 (134 mg, 0.346 mmol) in CH₂Cl₂ (10 ml) at 0° C. was perfused with HBr gas and then stirred at 0° C. for 2 hours. Following removal of HBr and CH₂Cl₂ in vacuo, the residue was taken up in EtOAc and successively washed twice with saturated NaHCO₃ solution, once with H₂O and once with brine. The resulting solution was dried (MgSO₄) and concentrated to leave the crude title compound as a brown oil. This was subjected to flash chromatography on silica gel using EtOAc as eluant. Fractions containing only the desired product were combined and concentrated to leave a pale tan oil (23 mg, 23%).

$^1$H NMR: δ 7.28–7.20 (m, 3 H), 7.09–7.03 (m, 1 H), 6.67 (s, 1 H), 4.82 (t, J=3 Hz, 1 H), 2.65 (br s, 1 H), 2.56 (dt, J=15, 3 Hz, 1 H), 2.42 (s, 3 H), 2.12–2.04 (m, 2 H), 1.94 (s, 3 H), 1.90–1.79 (m, 1 H).

The free title compound was taken up in MeOH and treated with a solution of HCl in methanol. After removal of the solvent and excess HCl in vacuo, the residue was azeotroped twice with ether to leave a white solid. This was dissolved in H₂O. The solution was filtered through a 22 μm Millipore filter and freeze-dried to yield the hydrochloride salt as a white solid (18 mg).

MS: m/z (relative percent) 287 (100). Exact mass calculated for $C_{16}H_{17}NS_2$: 287.0802. Found: 287.0763.

EXAMPLE 15

2-Bromo-11-methyl-4,5,6,11-tetrahydrobenzo[6,7]cycloocta[1,2-b]thiophen-6,11-imine-12-carboxylic acid-1,1-dimethylethyl ester and 2-bromo-11-methyl-4,5,6,11-tetrahydrobenzo[6,7]cycloocta[1,2-b]thiophen-6,11-imine To a solution of the compound of Example 10 (146 mg, 0.428 mmol) in CH₂Cl₂ (4 ml) and AcOH (4.4 ml) at 0° C. was added bromine (22 μl, 0.427 mmol). The mixture was stirred at 0° C. for 2 hours and then at room temperature overnight. Following removal of the solvents in vacuo, the residue was taken up in EtOAc and successively washed twice with saturated NaHCO₃ solution, once with H₂O and once with brine. The solution was dried (Na₂SO₄) and concentrated to leave a brown oil. This was subject to flash chromatography on silica gel using EtOAc as eluant. Eluted first was the carbamate, an oil (34 mg, 19%) upon removal of solvent.

$^1$H NMR: (partial) δ 7.30–7.20 (m, 3 H), 7.06–7.00 (m, 1H), 6.59 (s, 1 H), 5.36 (br, s, 0.6 H), 5.30 (br, s, 0.4 H), 2.23 (s, 1.2 H), 2.14 (s, 1.8 H), 1.44 (s, 3.6 H), 1.37 (s, 5.4 H).

The more polar amine (also an oil) was subsequently eluted.

$^1$H NMR: δ 7.33–7.24 (m, 3 H), 7.13–7.07 (m, 1H), 6.68 (s, 1 H), 4.84 (t, J=3 Hz, 1 H), 2.61 (dt, J=15, 3 Hz, 1 H), 2.49 (br s, 1 H), 2.18–2.08 (m, 2 H), 1.96 (s, 3 H), 1.94–1.84 (m, 1 H).

The free amine was taken up in MeOH and treated with a solution of HCl in methanol. After removal of the solvent and excess HCl in vacuo, the residue was azeotroped three times with ether to leave a white solid. This was dissolved in H₂O (5 ml). The solution was filtered through a 22 μm Millipore filter and freeze-dried to yield the hydrochloride salt as a white solid (29 mg, 19%).

MS: m/z (relative percent) 321 (100), 240 (97). Exact mass calculated for $C_{15}H_{14}\,^{81}BrNS$: 321.0010. Found: 321.0050.

EXAMPLE 16

2-Chloro-11-methyl-4,5,6,11-tetrahydrobenzo[6,7]-cycloocta[1,2-b]thiophen-6,11-imine To a solution of the carbamate of Example 15 (33 mg, 0.079 mmol) in dry DMF (1 ML) was added anhydrous CuCl (23 mg, 0.237 mmol). The solution was heated at gentle reflux overnight. After cooling, the solution s diluted with H₂O and extracted three times with EtOAc. The combined organic extracts were washed twice with H₂O and twice with brine. The solution was dried over Na₂SO₄ and concentrated to afford a brown oil. This was subjected to flash chromatography on silica gel using ethyl acetate as eluant. Fractions containing only the desired product were combined and concentrated in vacuo to leave the title compound as a pale tan oil. The amine was taken up in MeOH and treated with a solution of HCl in methanol. After removal of the solvent and excess HCl in vacuo, the residue was azeotroped twice with ether to leave a white solid. This was dissolved in H₂O (5 ml). The solution was filtered through a 22 μm Millipore filter and freeze-dried to yield the hydrochloride salt as a white solid (7 mg, 28%).

MS: m/z (relative percent) 275 (100), 240 (28). Exact mass calculated for $C_{15}H_{14}\,^{35}ClNS$: 275.0514. Found: 275.0420.

EXAMPLE 17

11-Methyl-6,11-dihydrobenzo[6,7]cycloocta[1,2-b]thiophen-6,11-imine-12-carboxylic acid-2,2,2-trichloroethyl ester A suspension of N-bromosuccinimide (210 mg, 1.17 mmol) in CCl₄ (12 ml) was brought to reflux. Azobisisobutyronitrile (10 mg) was then added followed shortly thereafter by a solution of the compound of Example 8 (486 mg, 1.17 mmol) in CCl₄. Heating at reflux was continued for 0.25 hour. The mixture was cooled and filtered through diatomaceous earth [Celite (trademark)] washing with ether. The filtrate was concentrated to leave an oil containing some solid (succinimide). Ether was added and the mixture was again filtered to remove the solid. After removal of the solvent in vacuo the oil residue (still containing solid) was taken up in toluene (55 ml) and treated with 1,8-diazobicyclo [5.4.0]undec-7-ene (DBU) (700 mg, 4.59 mmol). The resulting solution was then heated at reflux for 0.5 hour. During this period, a dark oil formed on the walls of the flask. After cooling, the toluene solution was decanted from the flask, washing with ether. The residue remaining in the flask was dissolved in H₂O and the resulting solution was extracted with ether. The ether phase was washed with brine, combined with the toluene solution and concentrated in vacuo. The crude oily product was then subjected to flash chromatography on two successive silica gel columns. The first column utilized 14% EtOAc/hexanes as eluant and served to remove unreacted DBU from the mixture. The second column was carefully run using 5% EtOAc/hexanes as eluant and successively separated the two major products of the reaction. The less polar product (144 mg, 21%) was identified as 11-methyl-6,11-dihydrobenzo[6,7]cycloocta[1,2-b]thiophene-6,11-imine-12-carboxylic acid-2,2,2-trichloro ethyl carbamate and was set aside. The more polar component (205 mg, 36%) was identified as the title compound and was carried on to the next step. Both products were oils.

$^1$H NMR: δ 7.28–7.24 (m, 3 H), 7.14–7.10 (m, 1 H), 6.99 (d, J=5 Hz, 0.6 H), 6.95 (d, J=5 Hz, 0.4 H), 6.77–6.74 (m, 1 H), 6.31–6.22 (m, 2 H), 5.72–5.67 (m, 1 H), 4.76–4.59 (m, 2 H), 2.37 (s, 0.4 H), 2.36 (s, 0.6 H).

EXAMPLE 18

11-Methyl-6,11-dihydrobenzo[6,7]cycloocta[1,2-b]thiophen-6,11-imine

To a solution of the compound of Example 17 (205 mg, 0.49 mmol) in glacial acetic acid (7 ml) was added zinc powder (700 mg, 6.1 mmol). The mixture was stirred under nitrogen in an oil bath at 55° C. for 7 hours and then cooled to room temperature. The mixture was filtered through diatomaceous earth [Celite (trademark)] (washing with ether) to remove excess zinc and concentrated. The oily residue was diluted with ether and washed with saturated NaHCO₃ solution. The solution was dried (Na₂SO₄) and concentrated in vacuo. The crude product was subjected to flash chromatography on silica gel using EtOAc as eluant. Fractions containing the title compound were combined and concentrated to afford a light brown oil (95 mg, 81%).

$^1$H NMR: δ 7.25–7.20 (m, 3 H), 7.13–7.08 (m, 1 H), 6.97 (d, J=5 Hz, 1 H), 6.81 (d, J=5 Hz, 1 H), 6.37–6.27 (m, 2 H), 5.02 (d, J=5 Hz, 1 H), 2.29 (br s, 1 H), 2.01 (s, 3 H).

The hydrobromide salt was prepared by addition of a solution of HBr in ether to a solution of the amine in ether at 0° C. and recrystallized from MeOH/ether; m.p. 287°–289° C.

MS: m/z (relative percent) 239 (100), 224 (28), 212 (44), 197 (41). Exact mass calculated for C₁₅H₁₃NS: 239.0769. Found: 239.0728.

Analysis calculated for C₁₅H₁₄BrNS: C, 56.26; H, 4.41; N, 4.37. Found: C, 55.91; H, 4.35; N, 4.38.

EXAMPLE 19

11,12-Dimethyl-4,5,6,11-tetrahydrobenzo[6,7]cycloocta-[1,2-b]thiophen-6,11-imine To a solution of the compound of Example 9 (75 mg, 0.311 mmol) and fumaric acid (36 mg, 0.31 mmol) in CH₃CN (2.5 ml) was added 37% formaldehyde solution (120 μl) and sodium cyanoborohydride (28 mg, 0.45 mmol). The mixture was stirred at room temperature for 4 hours and then made basic with 1N NaOH solution. The solution was extracted twice with EtOAc and the combined extracts were washed with brine, dried (Na₂SO₄) and concentrated to leave a viscous oil. This was subjected to flash chromatography on silica gel using 25% EtOAc/hexanes as eluant. Fractions containing only the title compound were combined and concentrated to leave an oil (46 mg, 51%).

$^1$H NMR: δ 7.24–7.16 (m, 3 H), 7.06–7.02 (m, 1 H), 6.88 (d, J=5 Hz, 1 H), 6.63 (d, J=5 Hz, 1 H), 4.55 (br s, 1 H), 2.47 (br d, J=15 Hz, 1 H), 2.37–2.25 (m, 1 H), 2.22 (s, 3 H), 1.88 (s, 3 H), 1.76–1.57 (m, 2 H).

The hydrochloride salt was prepared in a mixture of isopropanol/ether (37 mg); m.p. greater than 240° C.

MS: m/z (relative percent) 255 (100), 240 (88), 158 (82).

EXAMPLE 20

N-t-Butyldiphenylsilyl-4-fluoro-αmethyl-benzenemethanamine

To a solution of racemic 4-fluoro-α-methylbenzenemethanamine (2.95 g, 21.2 mmol) and triethylamine (4.3 mL, 30.9 mmol) in acetonitrile (75 mL) in a flame-dried flask under nitrogen was added dropwise t-butyl-chlorodiphenylsilane (5.5 mL, 21.1 mmol). The mixture was stirred at room temperature overnight and then filtered to remove the insoluble white precipitate (triethylamine hydrochloride). After removal of the solvent in vacuo, the crude product was taken up in ether and washed sequentially with H₂O, saturated NaHCO₃ solution and brine. The solution was dried (Na₂SO₄/K₂CO₃) and concentrated to leave a clear oil which was distilled under high vacuum. The major fraction consisting of the pure title compound (3.8 g, 47%) distilled from 123° to 143° C. at 0.15 mm Hg.

$^1$H NMR: δ 7.72–7.65 (m, 2 H), 7.50–7.44 (m, 2 H), 7.40–7.28 (m, 4 H), 1.33 (d, J=6.5 Hz, 3 H), 1.30 (br s, 1 H), 1.04 (s, 9 H).

EXAMPLE 21

6-[2-(1-Aminoethyl)-4-fluorophenyl]-4H-cyclopenta[b]thiophene

A solution of the compound of Example 20 (3.8 g, 0.1 mmol) and N,N,N',N'-tetramethylethylenediamine (0.75 mL, 5.0 mmol) in dry ether (70 ml) was cooled to 0° C. and treated with a solution of n-BuLi (2.5M) in hexane (8.0 mL, 20 mmol). The mixture was stirred at 0° C. for 0.25 hour and then at room temperature for an additional 3 hours. At this point the mixture was cooled to −78° C. A solution of the compound of Example 5 (1.4 g, 10.0 mmol) in dry THF (15 ml) was then added dropwise and the resulting mixture was stirred at −78° to −60° C. over 1 hour. The reaction was quenched by addition of saturated NH₄Cl solution and was allowed to warm to room temperature. The mixture was diluted with ether and H₂O. The ether layer was separated and concentrated to leave an oil which was taken up in a mixture of 1N HCl (70 mL) and THF (105 mL). The resulting solution was stirred at room temperature overnight. The mixture was then diluted with H₂O and extracted twice with ether. The extracts were set aside for later recovery of unreacted compound of Example 5 while the aqueous layer was made basic by addition of solid NaOH and extracted twice again with ether. These extracts were combined, dried (Na₂SO₄) and concentrated in vacuo to leave a dark oil. This was placed under high vacuum and warmed to remove 4-fluoro-α-methyl-benzenemethanamine. The crude product was then subjected to flash chromatography on SiO₂ using successively CHCl₃ and 2% MeOH/CHCl₃ as eluants. Fractions containing the title compound were combined and concentrated to afford an oil, 540 mg (21%).

¹H NMR: δ 7.59 (dd, J=6, 9.5 Hz, 1 H), 7.21 (d, J=5 Hz, 1 H), 7.09 (d, J=5 Hz, 1 H) 7.08–7.04 (m, 2 H), 6.33 (m, 0.25 H), 4.42 (q, J=6.5 Hz, 1 H), 3.39 (s, 2 H), 1.60 (br s, 2 H), 1.30 (d, J=6.5 Hz, 3 H).

EXAMPLE 22

8-Fluoro-11-methyl-4,5,6,11-tetrahydrobenzo[6,7]-cycloocta[1,2-b]thiophen-6,11-imine To a soluton of the compound of Example 21 (540 mg, 2.08 mmol) and 4-dimethylaminopyridine (366 mg, 3.0 mmol) in $CH_2Cl_2$ (50 mL) at 0° C. was added 2,2,2-trichloroethylchloroformate (0.43 mL, 3.12 mmol). After stirring at 0° C. for 1 hour, HBr gas was bubbled through the solution to achieve saturation. Stirring at 0° C. was continued for an additional 0.5 hour at which point the solvent was removed in vacuo. The residue was subjected to flash chromatography on silica gel using $CHCl_3$ as eluant. All product fractions were combined and concentrated to leave an oil. The ¹H NMR spectrum of this material showed it to consist of a mixture (about 1:1) of 8-fluoro-11-methyl-4,5,6,11-tetrahydrobenzo[6,7]cycloocta[1,2-b]thiophen-6,11-imine-1,2-carboxylic-2,2,2-trichloroethyl ester and 6'-fluoro-4,5,2',3'-tetrahydro-spiro[6H-cyclopenta[b]-thiophene-6,1'-[1H]isoindole]-2'-carboxylic acid-2,2,2-trichloroethyl ester (the major components of the reaction). The mixture was again taken up in $CH_2Cl_2$ (50 ml). The resulting solution was cooled to 0° C. and saturated with HBr gas. After stirring at room temperature for a further 6 hours, the volatiles were removed in vacuo. The ¹H NMR spectrum at this point showed that little further rearrangement to 8-fluoro-11-methyl-4,5,6,11-tetrahydrobenzo[6,7]cycloocta-[1,2-b]thiophen-6,11-imine-12-carboxylic-2,2,2-trichloroethyl ester had occurred. The residue was subjected to flash chromatography on silica gel using $CHCl_3$ as eluant. Separation of the major components of the reaction was not successful. The oily mixture (460 mg, 51%) was thus dissolved in glacial acetic acid (50 ml) and treated with zinc powder (653 mg, 10 mmol) to effect removal of the 2,2,2-trichloroethyloxycarbonyl group. The mixture was stirred under nitrogen in an oil bath at 60° C. for overnight and then cooled to room temperature. Excess zinc was removed by filtration through diatomaceous earth [Celite (trademark)] (washing with $CH_2Cl_2$) and the solvents were evaporated in vacuo. The oily residue was dissolved in $CH_2Cl_2$ and washed with saturated $NaHCO_3$ solution and brine. The solution was dried ($MgSO_4$) and concentrated in vacuo. The crude product mixture was subjected to flash chromatography on silica gel using EtOAc as eluant. Separation of the title compound and 6'-fluoro-4,5,2',3'-tetrahydro-spiro[6H-cyclopenta[b]thiophene-6,1'-[¹H]isoindole] was achieved. Fractions containing the title compound were combined and concentrated to afford an oil (54 mg, 10%). Fractions containing the aforementioned isoindole also yielded an oil (86 mg, 16%).

¹H NMR δ 7.01–6.90 (m, 3 H), 6.88 (d, J=5 Hz, 1 H), 6.67 (d, J=5 Hz, 1 H), 4.76 (t, J=3 Hz, 1 H), 2.66 (dt, J=15, 3 Hz, 1 H), 2.17 (br s, 1 H), 2.08–1.90 (m, 3H), 1.94 (m, 3 H).

A sample of the hydrochloride salt was prepared by addition of a solution of HCl in ether to an ice cold solution of the amine in ether. The precipitate was recrystallized from a mixture of ether and 2-propanol; m.p. greater than 250° C.

MS: m/z (relative percent) 259 (100), 244 (30). Exact mass calculated for $C_{15}H_{14}FNS$: 259.0831. Found: 259.0841.

Analysis calculated for $C_{15}H_{15}ClFNS$: C, 60.91; H, 5.11; N, 4.74. Found: C, 60.68; H, 5.04; N, 4.71.

EXAMPLE 23

N-t-Butyldiphenylsilyl-α,4-dimethyl-benzenemethanamine

To a solution of racemic α,4-dimethyl-benemethanamine (4.00 g, 30.0 mmol) and triethylamine (6.1 mL, 43.8 mmol) in acetonitrile (100 mL) in a flame-dried flask under nitrogen was added dropwise t-butylchlorodiphenylsilane (7.7 mL, 29.6 mmol). The mixture was stirred at room temperature overnight and then filtered to remove the insoluble white precipitate (triethylamine hydrochloride). After removal of the solvent in vacuo, the crude product was taken up in ether and washed sequentially with $H_2O$, saturated $NaHCO_3$ solution and brine. The solution was dried ($Na_2SO_4$/$K_2CO_3$) and concentrated to leave a clear oil which was distilled under high vacuum. The major fraction consisting of the title compound (6.7 g, 60%) distilled from 134° to 165° C. at 0.1 mm Hg.

¹H NMR: δ 7.75–7.72 (m, 2 H), 7.57–7.54 (m, 2 H), 7.41–7.22 (m, 6 H), 7.12–7.04 (m, 4 H), 3.98–3.88 (m, 1 H), 2.35 (s, 3 H), 1.36 (br s, 1 H), 1.31 (d, J=6.5 Hz, 3 H), 1.03 (s, 9 H).

EXAMPLE 24

6-[2-(1-Aminoethyl)-4-methylphenyl]-4H-cyclopenta[b]-thiophene

A solution of compound of Example 23 (3.7 g, 9.9 mmol) and N,N,N',N'-tetramethylethylenediamine (0.75 mL, 5.0 mmol) in dry ether (70 ml) was cooled to 0° C. and treated with a solution of n-BuLi (2.5M) in hexane (8.0 mL, 20.0 mmol). The mixture was stirred at 0° C. for 0.25 hour and then at room temperature for an additional 3 hours. At this point the mixture was cooled to −78° C. A solution of 4,5-dihydro-6H-cyclopenta[b]thiophen-6-one (1.40 g, 10.1 mmol) in dry THF (15 ml) was then added dropwise and the resulting mixture was stirred at −78° to −60° C. over 1 hour. The reaction was quenched by addition of saturated $NH_4Cl$ solution and was allowed to warm to room temperature. The mixture was diluted with ether and $H_2O$. The ether layer was separated and concentrated to leave an oil which was taken up in a mixture of 1N HCl (70 mL) and THF (105 mL). The resulting solution was stirred at room temperature overnight. Following removal of most of the THF in vacuo, the solution was extracted twice with ether. The extracts were set aside for later recovery of unreacted 4,5-dihydro-6H-cyclopenta[b]-thiophen-6-one while the aqueous layer was made basic by addition of solid NaOH and extracted twice again with ether. These extracts were combined, dried ($Na_2SO_4$) and concentrated in vacuo to leave an oil. This was placed under high vacuum and warmed to remove α,4-dimethyl-benzenemethanamine. Following flash chromatography on silica gel using EtOAc as eluant, the title compound was isolated as an oil (180 mg, 7%).

¹H NMR: δ 7.49 (d, J=8 Hz, 1 H), 7.22–7.18 (m, 2 H), 7.08 (d, J=4.5 Hz, 1 H), 6.36 (t, J=2 Hz, 1 H), 4.41 (q, J=6.5 Hz, 1 H), 3.40 (d, J=2 Hz, 2 H), 2.35 (s, 3 H), 1.33 (d, J=6.5 Hz, 3 H).

EXAMPLE 25

8,11-Dimethyl-4,5,6,11-tetrahydrobenzo[6,7]cycloocta-[1,2-b]thiophen-6,11-imine-12-carboxylic acid-2,2,2-trichloroethyl ester To a solution of the compound of Example 24 (180 mg, 0.705 mmol) and 4-dimethylaminopyridine (122 mg, 1.0 mmol) in $CH_2Cl_2$ (15 mL) at 0° C. was added 2,2,2-trichloroethylchloroformate (0.14 mL, 1.0 mmol). After stirring at 0° C. for 0.25 hour, HBr gas was bubbled through the solution to achieve saturation. Stirring at 0° C. was continued for an additional 0.5 hour at which point the solvent was removed in vacuo. The residue was subjected to flash chromatography on silica gel using 10% EtOAc/hexane as eluant. Fractions containing the title compound were combined, concentrated to leave an oil (230 mg, 76%). The $^1$H NMR spectrum of this material showed it to be slightly impure.

$^1$H NMR: δ (m, 4 H), 6.63–6.59 (m, 1 H), 5.48 (br s, 0.6 H), 5.45 (br s, 0.4 H), 4.82 (d, J=12 Hz, 0.4 H), 4.74 (d, J=12 Hz, 0.6 H), 4.66 (d, J=12 Hz, 0.6 H), 4.61 (d, J=12 Hz, 0.4 H), 2.65–2.43 (m, 2 H), 2.37 (s, 3 H), 2.33 (s, 1.2 H), 2.32 (s, 1.8 H), 2.03–1.78 (m, 2 H).

EXAMPLE 26

8.11-Dimethyl-4,5,6,11-tetrahydrobenzo[6,7]cycloocta-[1,2-b]thiophen-6,11-imine

To a solution of the carbamate (230 mg, 0.534 mmol) in glacial acetic acid (20 ml) was added zinc powder (326 mg, 5.0 mmol). The mixture was stirred under nitrogen in an oil bath at 50° C. overnight and then cooled to room temperature. The mixture was filtered through diatomaceous earth [Celite (trademark)] (washing with $CH_2Cl_2$) to remove excess zinc and concentrated. The oily residue was diluted with $CH_2Cl_2$ and washed with saturated $NaHCO_3$ solution. The solution was dried ($MgSO_4$) and concentrated in vacuo. The crude product was subjected to flash chromatography on silica gel using 20% EtOac/hexanes as eluant. Fractions containing the desired product were combined and concentrated to afford an oil.

$^1$H NMR: δ 7.07–7.01 (m, 2 H), 6.93 (d, J=8 Hz, 1 H), 6.86 (d, J=5 Hz, 1 H), 6.66 (d, J=5 Hz, 1 H), 4.75 (t, J=3 Hz, 1 H), 2.63 (dt, J=15, 3 Hz, 1 H), 2.34 (s, 3 H), 2.10–1.85 (m, 4 H), 1.94 (s, 3 H).

The amine was converted into its hydrochloride salt by careful addition of a solution of HCl in ether to a solution of the amine in ether at 0° C. The precipitate was recrystallized from a MeOH/ether; m.p. greater than 250° C. The yield was 30 mg (19%).

MS: m/z (relative percent) 255 (100). Exact mass calculated for $C_{16}H_{17}NS$: 255.1082. Found: 255.1090.

Analysis calculated for $C_{16}H_{18}ClNS$: C, 65.85; H, 6.22; N, 4.80. Found: C, 65.11; H, 6.11; N, 4.59.

EXAMPLE 27

Resolution of 11-methyl-4,5,6,11-tetrahydrobenzo-[6,7]cycloocta[1,2-b]thiophen-6,11-imine A solution of the compound of Example 9 (202 mg, 0.837 mmol) in anhydrous tetrahydrofuran (10 mL) was added dropwise to a stirred solution of (R)-(−)-(1-naphthyl)ethyl isocyanate (147 μL, 0.838 mmol) in anhydrous tetrahydrofuran (10 mL). The resulting mixture was stirred at room temperature overnight. The solvent was then removed in vacuo to leave a viscous brown oil which was crystallized from acetonitrile. A white solid (138 mg) was collected by filtration while the filtrate was concentrated to yield a tan foam (233 mg). By HPLC (high pressure liquid chromatography) analysis, the solid was shown to be enriched in one diastereomeric urea derivative of the title compound (diastereomer A) while the foam was shown to be enriched in the other diastereomer (diastereomer B). The solid was recrystallized from hot acetonitrile (8 mL) and the recrystallized material was triturated with acetonitrile (8 mL) at room temperature for 2 minute. Pure diastereomer A (113 mg) was then collected by filtration. Filtrates from the recrystallization/trituration of diastereomer A were combined with the tan foam above and concentrated. The residue, in about 30 mg batches, was subjected to preparative scale HPLC using a Dynamax (trademark) 21.4 mm×25 mm 300A 12 μm $C_{18}$ column and 1:1 acetonitrile/water as the mobile phase run at 15 mL/minute. Material eluting between 43.3 and 50 minutes was collected, combined and concentrated to leave pure diastereomer B as a white foam (74 mg). Subsequently eluted less pure fractions of diastereomer B were again subjected to preparative HPLC as before to provide, after concentration, an additional amount of pure diastereomer B (20 mg).

Diastereomer A $^1$H NMR (CDCl$_3$) δ 7.94–7.92 (m, 1 H), 7.72–7.68 (m, 1 H), 7.60 (d, J=8.5 Hz, 1H), 7.38–7.32 (m, 2 H), 7.23–7.16 (m, 4 H), 6.98–6.94 (m, 1 H), 8.81 (d, J=8 Hz, 1 H), 6.64 (d, J=5 Hz, 1 H), 6.43 (d, J=5 Hz, 1 H), 5.72–5.63 (m, 1 H), 5.41 (s, 1 H), 4.86 (d, J=7 Hz, 1H), 2.51–2.43 (m, 1 H), 2.36–2.27 (m, 1H), 2.19 (s, 3 H), 1.83–1.62 (m, 2 H), 1.51 (d, J=7 Hz, 3 H).

Diastereomer B $^1$H NMR (CDCl$_3$) δ 7.94 (d, J=7.5 Hz, 1 H), 7.76 (d, J=8.5 Hz, 1 H), 7.70 (d, J=8.5 Hz, 1 H), 7.42–7.32 (m, 4 H), 7.20–7.12 (m, 3 H), 6.99–6.94 (m, 1 H), 6.92 (d, J=5 Hz, 1 H), 6.63 (d, J=5 Hz, 1H), 5.74–5.65 (m, 1 H), 5.31 (s, 1H), 4.67 (d, J=7 Hz, 1H), 2.50–2.43 (m, 1 H), 2.25–2.10 (m, 1H), 2.14 (s, 3H), 1.74–1.62 (m, 2H), 1.43 (d, J=7 Hz, 3 H).

Diastereomer A (113 mg, 0.26 mmol) was dissolved in a mixture of p-dioxane (30 mL) and water (10 mL). After addition of 1N NaOH solution (2.32 mL, 2.32 mmol), the mixture was heated at reflux for 6 days and then cooled. The solvents were removed in vacuo to leave a residue which was subjected to flash chromatography on silica gel using ethyl acetate as eluant. Fractions containing the desired product [(+)-11-methyl-4,5,6,11-tetrahydrobenzo[6,7]cycloocta[1,2-b]-thiophen-6,11-imine] were combined and concentrated to provide an oil (53 mg, 85%), [α]$_D$= +234.9°.

Diastereomer B (94 mg, 0.215 mmol) was dissolved in a mixture of p-dioxane (23 mL) and water (8 mL). After addition of 1N NaOH solution (1.93 mL, 1.93 mmol), the mixture was heated at reflux for 6 days, and then cooled. The solvents were removed in vacuo to leave a residue which was subjected to flash chromatography on silica gel using ethyl acetate as eluant. Fractions containing the desired product [(−)-11-methyl-4,5,6,11-tetrahydrobenzo[6,7]cycloocta-[1,2-b]thiophen-6,11-imine] were combined and concentrated to provide an oil (40 mg, 77%), [α]$_D$=257.9°.

The (+)- and (−) enantiomers each displayed $^1$H NMR. spectra identical to the racemic material and were separately converted to their respective hydrochloride salts as described in Example 9.

The (+)-enantiomer was found to be approximately eight times as active as the (−)-enantiomer when tested in the $^3$H-TCP binding assay.

EXAMPLE 28

P2 membranes from rat forebrain were suspended in 5 mM tris(hydroxymethyl)aminomethane hydrochloride buffer (pH 7.4). A solution of the test compound in H$_2$O or DMSO/H$_2$O was added followed by a solution of $^3$H-TCP The mixture was incubated for 20 minutes at 30° C. and then injected onto a glass fiber filter. The filters were washed with cold buffer and placed in vials for subsequent liquid scintillation spectrometry. IC$_{50}$ were calculated from the amount of tritium label retained on the filters. The title compounds of Examples 9, 22 and 26 were tested in this $^3$H-TCP binding assay and were found to display an IC$_{50}$ of no greater than 40 nanomolar. In this assay, the title compounds of Examples 4, 14, 15 (free amine), 16 and 18 were found to display an IC$_{50}$ of no greater than 2 micromolar.

We claim:

1. A compound of the formula

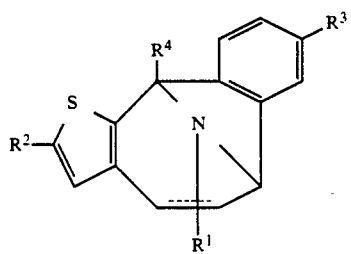

I wherein the broken line represents a saturated or an olefinic bond,

R$^1$ and R$^4$ are each hydrogen or C$_1$ to C$_6$ alkyl, and R$^2$ and R$^3$ are each hydrogen, C$_1$ to C$_6$ alkyl, halogen, C$_1$ to C$_6$ alkoxy or C$_1$ to C$_6$ alkylthio, with the proviso that when R$^2$ and R$^3$ are each hydrogen, halogen, or C$_1$ to C$_6$ alkoxy the broken line represents an olefinic bond, or a pharmaceutically acceptable salt thereof.

2. The compound of claim 1 wherein R$^4$ is methyl.

3. The compound of claim 1 wherein the broken line represents a saturated bond.

4. The compound of claim 1 wherein R$^1$ is hydrogen.

5. The compound of claim 4 wherein R$^4$ is methyl.

6. The compound of claim 1 wherein R$^3$ is hydrogen.

7. The compound of claim 3 wherein R$^1$, R$^2$, R$^3$ and R$^4$ are hydrogen.

8. The compound of claim 2 wherein the broken line represents a saturated bond.

9. The compound of claim 8 wherein R$^1$ and R$^3$ are each hydrogen.

10. The compound of claim 9 wherein R$^2$ is hydrogen.

11. The compound of claim 9 wherein R$^2$ is methyl.

12. The compound of claim 9 wherein R$^2$ is methylthio.

13. The compound of claim 9 wherein R$^2$ is chloro.

14. The compound of claim 8 wherein R$^3$ is methyl and R$^1$ and R$^2$ are hydrogen.

15. A compound of the formula

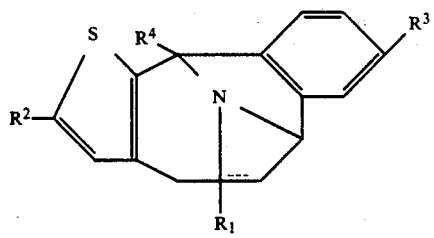

wherein the broken line represents a saturated or an olefinic bond,

R$^1$ is protecting group, R$^2$ is hydrogen, R$^3$ is hydrogen, fluorine or methyl, with the proviso that when R$^3$ is hydrogen or fluorine the broken line represents an olefinic bond, R$^4$ is hydrogen or methyl.

16. A compound of the formula

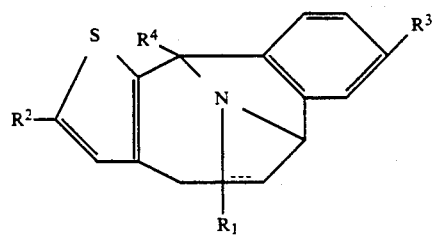

wherein R$^1$ is protecting group, R$^3$ is hydrogen, fluorine or methyl, R$^4$ is hydrogen or methyl.

17. The compound of claim 16 wherein R$^4$ is methyl and R$^3$ is hydrogen or wherein R$^4$ is methyl and R$^3$ is fluorine or wherein R$^3$ and R$^4$ are methyl.

18. A method for the treatment of cerebral ischemia, Alzheimer's disease or convulsions, comprising administering an amount of a compound of claim 1 that is effective in preventing neuronal damage following cerebral ischemia or during the progression of Alzheimer's disease or in preventing convulsions.

19. A pharmaceutical composition for the treatment of cerebral ischemia, Alzheimer's disease or convulsions, comprising an amount of a compound of claim 1 that is effective in preventing neuronal damage following cerebral ischemia or during the progression of Alzheimer's disease or in preventing convulsions and a pharmaceutically acceptable carrier.

20. A compound of claim 1, said compound being selected from the group consisting of:

11-methyl-4,5,6,11-tetrahydrobenzo[6,7]cycloocta[1,2-b]thiophen-6,11-imine;

8-fluoro-11-methyl-4,5,6,11-tetrahydrobenzo[6,7]cycloocta[1,2-b]thiophene-6,11-imine; and 8,11-dimethyl-4,5,6,11-tetrahydrobenzo[6,7]cycloocta[1,2-b]thiophene-6,11-imine.

* * * * *